(12) United States Patent
Van Snick et al.

(10) Patent No.: US 7,094,396 B2
(45) Date of Patent: Aug. 22, 2006

(54) METHOD FOR MAKING CYTOKINE SPECIFIC ANTIBODIES AND USES THEREOF

(75) Inventors: Jacques Van Snick, Wezembeek-Oppem (BE); Jean Christophe Renauld, Kraainem (BE); Mélisande Richard, Brussels (BE)

(73) Assignee: Ludwig Institiute for Cancer Research, New York, NY (US)

( * ) Notice: Subject to any disclaimer, the term of this patent is extended or adjusted under 35 U.S.C. 154(b) by 354 days.

(21) Appl. No.: 10/638,234

(22) Filed: Aug. 8, 2003

(65) Prior Publication Data

US 2004/0028650 A1     Feb. 12, 2004

Related U.S. Application Data

(62) Division of application No. 09/490,586, filed on Jan. 25, 2000, now Pat. No. 6,645,486.

(51) Int. Cl.
*A61K 38/20* (2006.01)

(52) U.S. Cl. ............... 424/85.2; 424/184.1; 424/185.1; 424/198.1

(58) Field of Classification Search ..................... None
See application file for complete search history.

(56) References Cited

U.S. PATENT DOCUMENTS 6,645,486 B1 * 11/2003 Van Snick et al. ......... 424/85.2

OTHER PUBLICATIONS

Callard and Gearing (1994) The Cytokine Factsbook. Academic Press Ltd. p. 79.*

* cited by examiner

*Primary Examiner*—Prema Mertz
(74) *Attorney, Agent, or Firm*—Fulbright & Jaworski (57) ABSTRACT

The methods of this invention relate to immunizing animals with conjugates of cytokines and a carrier to induce a prolonged high titre antibody response specific for the cytokine. This invention also relates to the treatment of pathological conditions, e.g., eosinophilia and allograft rejection, associated with the production of cytokines, in particular interleukins, e.g., IL-4, IL-5, IL-9, and IL-13, by immunization with the cytokine conjugates or by administration of antibodies specific for the cytokine. This invention also relates to compositions comprising the cytokine conjugates and the conjugates per se.

19 Claims, 5 Drawing Sheets

Figure 5

METHOD FOR MAKING CYTOKINE SPECIFIC ANTIBODIES AND USES THEREOF

RELATED APPLICATIONS

This application is a divisional of application Ser. No. 09/490,586 filed Jan. 25, 2000 now U.S. Pat. No. 6,645,486.

FIELD OF THE INVENTION

This invention relates to methods for making cytokine specific antibodies. This invention also relates to methods for inducing in an animal a high titre antibody response specific for the cytokine. This invention further relates to the treatment of pathological conditions, e.g., eosinophilia, associated with the production of the cytokines. In addition, this invention relates to cytokine conjugates per se and compositions comprising the cytokine conjugates.

BACKGROUND

Cytokines are involved in many biological functions and are major mediators of the immune response. They are associated with the initiation and progression of various autoimnimune diseases. For example, tumor necrosis factor α (TNFα), interferon γ (IFNγ) and interleukin-1 (IL-1) have been associated with diabetes and the destruction of islet cells, the elevated production of Th2 cytokines have been associated with asthma, and interleukin-12 (IL-12) has been associated with rhuematoid arthritis.

Interleukin-9 ("IL-9" hereafter), is a glycoprotein which has been isolated from both murine and human cells. See, e.g., U.S. Pat. No. 5,208,218, incorporated by reference. This reference also teaches isolated nucleic acid molecules encoding the protein portion of the molecule, and how to express it.

Since its discovery as a T- and mast cell-growth factor produced by Th2 cells, the physiological processes in which for IL-9 is known to have a role have been gradually expanded (Uyttenhove, et al., *Proc. Natl. Acad. Sci. USA* 85:6934–6938 (1988); Hültner, et al., *Eur. J. Immunol.* 20:1413–1416 (1990); and Gessner, et al., *Immunobiol.* 189:419–435 (1993)) (Renauld, J.-C., & Van Snick, J. (1998), The *Cytokine Handbook* 313–331). Prominent features, disclosed by analysis of transgenic mice overexpressing IL-9, include increased susceptibility to lymphomagenesis (Renauld, et al., *Oncogene* 9:1327–1332 (1994)), intestinal mastocytosis (Godfraind, et al., *J. Immunol.* 160:3989–3996 (1998)), expansion of the B-1 lymphocyte population (Godfraind, et al., *J. Immunol.* 160:3989–3996 (1998)), bronchial hyper-responsiveness (Temann, et al., *J. Exp. Med.* 188:1307–1320 (1998), and McLane, et al., *Am J. Resp. Cell. Mol.* 19:713–720 (1998)) and airway eosinophilia (Dong, et al., *Eur. J. Immunol.* 29:2130–2139 (1999)). In line with these observations, genetic analyses revealed a linkage between both IL-9 and IL-9 receptor (IL-9R) genes to human asthma (Holroyd, et al., *Genomics* 52:233–235 (1998) and Marsh, et al. *Science* 264:1152–1156 (1994)), a finding that was confirmed with respect to IL-9 in murine models (Nicolaides, et al., *Proc. Natl. Acad. Sci. USA*, 94: 13175–13180 (1997)).

Various uses of IL-9 are disclose in, e.g., U.S. Pat. No. 5,164,317 (proliferation of mast cells); U.S. Pat. Nos. 5,246,701 and 5,132,109 (enhancing production of IgG and inhibiting production of IgE), in addition to its first recognized utility, which is as a T cell growth factor. Exemplary of the vast scientific literature on IL-9 are Van Snick, et al, *J. Exp. Med.* 169(1): 363–368 (1989) (cDNA for the murine molecule, then referred to as P40). Houssiau, etal, *J. Immunol* 148, (10): 3147–3151(1992) (IL-2 dependence of IL-9 expression in T lymphocytes). Renauld, et al, *Oncogene* 9(5):1327–1332 (1994) (effect on thymic lymphomas); Renauld, et al, *Blood* 85(5):1300–1305 (1995) (anti-apoptotic factor for thymic lymphoma); U.S. Pat. No. 5,830,454 (treatments of cell mediated autoimmune disorders); and U.S. Pat. No. No. 5,935,929 (treating or preventing interstitial lung disease). Review articles may be found at, e.g., Renauld, et al, *Cancer Invest*, 11(5): 635–640 (1993); Renauld, et al, *Adv. Immunol* 54:79–97 (1993).

While detrimental in asthma, elevated production of Th2 cytokines has been reported to correlate with resistance to certain parasite infections (Finkelman, et al., *Annu. Rev. Immunol.*, 15:505–533 (1997)). IL-9, for example, was found to enhance mouse resistance to infection with the caecal dwelling nematode *T.muris* (Faulkner, et al., *Infect. Immun.*, 66:3832–3840(1998)). This resistance was associated with high IgE and IgG1 levels, as well as with pronounced intestinal mastocytosis.

The absence of T cell help has previously been suggested to be crucial for B cell tolerance toward self-proteins (Dalum, et al., *J. Immunol.*, 157 ; 4786–4804 (1996)). Using bovine luteinizing hormone (LH) as a self protein coupled to ovalbumin (OVA), Johnson, et al. (*J. Anim. Sci.*, 66, 719–726 (1988)) were able to induce high titers of autoantibodies against LH, causing cows to become anestrous. Similarly, a vaccine that prevents pregnancy in women was developed by coupling human chorionic gonadotropin and ovine luteinizing hormone to tetanus and diphtheria toxoids (Talwar, et al., *Proc. Natl. Acad. Sci. USA*, 91:8532–8536 (1994)). More recently, immunization with a fusion protein of an OVA epitope and mouse TNFα was found to prevent experimental cachexia and collagen-induced arthritis in mice (Dalum, et al., *Nature Biotechnology*, 17:666–669 (1999)).

Earlier attempts to generate autoantibodies capable of regulating biological processes, were successfully carried out mainly with hormones (Johnson, et al., *J. Anim. Sci.*, 66:719–726 (1988) and Talwar, et al., *Proc. Natl. Acad. Sci. USA*, 91:8532–8536 (1994)), hormone receptors (Chackerian, et al. *Proc. Natl. Acad. Sci. USA*, 96:2773–2778 (1999)) or cellular components (Dong, et al., *J. Exp. Med.*, 179:1243–1252 (1994) and Dalum, et al., *Mol. Immunol.*, 34:1113–1120 (1997)). These observations were recently extended to cytokines with reports of anti-IFNα induction in AIDS patients (Zagury, et al., *Biomed. Pharmacother*, 53:90–92 (1999)) and of anti-TNFα vaccination in mice, the latter preventing cachexia and rheumatoid arthritis (Dalum, et al., *Nature Biotechnology*, 17:666–669 (1999)).

SUMMARY OF THE INVENTION

This invention is directed to methods for making cytokine specific antibodies, particularly antibodies specific for interleukins. This invention is also directed to a method for preventing or treating a pathological condition associated with the production of a cytokine by immunizing an animal with a conjugate of the cytokine and a carrier. Preferably, the cytokine is an interleukin, more preferably, IL-4, IL-5, IL-9, or IL-13 and most preferably the interleukin is IL-9. The IL-9 may be a mammalian IL-9, inparticular a murine orhuman IL-9, preferably a recombinant form or a portion of the IL-9 molecule sufficient to provoke a response.

The invention is also directed to a method for producing prolonged high titre antibodies specific for the cytokine by immunizing a subject with conjugates of the cytokine and a carrier. Preferably, the high titre persists for at least 6 months after the subject is immunized with the conjugate, more preferably, the high titre persists for at least 9 months after the immunization and most preferably, at least 12 months after the immunization.

This invention is further directed to conjugates of a carrier and the cytokine, or portions thereof, and to compositions comprising the conjugates. Preferably, the cytokine is an interleukin and the carrier is ovalbumin (OVA), a substituted OVA, a keyhole limpet hemocyanin (KLH), an acetylated BSA or a pertussis toxin. More preferably the conjugate comprises an interleukin selected from the group consisting of IL-4, IL-5, IL-9 or IL-13, and most preferably comprises IL-9. Especially preferred is a conjugate of IL-9 and ovalbumin. The interleukin may be a recombinant interleukin or an interleukin modified to permit or enhance its conjugation to a carrier.

Those of skill in the art appreciate that many methods are suitable for conjugating a carrier and a conjugation partner. The partners in a conjugate may be treated with a crosslinking agent, e.g., glutaraldehyde, carbodilmide or bisdiazobenzidine. The conjugation partners be also be modified to permit or enhance the formation of conjugates. For example, the carrier may be substituted with maleimide, e.g., a maleimide-substituted OVA, so that it is suitable for forming a conjugate with an interleukin having free SH groups, e.g, a irminothyolane-treated IL-9.

The invention is also directed to methods for producing polyclonal and monoclonal antibodies specific for a cytokine comprising the step of immunizing an animal with a conjugate of the cytokine and a carrier, particularly ovalburnin. In particular the invention is directed to methods for producing monoclonal antibodies specific for IL-9 which comprises immunizing an animal with an IL-9 conjugate, in particular a conjugate of IL-9 and ovalbumin. The monoclonal and polyclonal antibodies of this invention are useful for the treatment of an animal having a disorder that depends at least in part on the production of IL-9.

The invention is also directed to the treatment of a pathological condition or disorder in an animal where the condition or disorder is dependent, at least in part, on the expression of a cytokine, preferably an interleukin, by administering to an animal in need thereof polyclonal or monoclonal antibodies specific to the cytokine. The ability of IL-9 autoantibodies to inhibit the resistance of mice to parasite infection and to abrogate blood eosinophilia is disclosed for the first time herein. Thus a particularly preferred method of this invention is a method for the treatment of eosinophilia and disorders associated with eosinophilia, e.g., allograft rejection, by administering antibodies that are specific for IL-9 to an animal in need thereof. Preferably the animal is a mammal, more preferably the animal is a human.

The methods of this invention also relate to assaying the in vivo effects of long term inhibition of the activity of specific interleukins and for assaying the effectiveness of agents for treating disorders associated with the long term inhibition of an interleukin. For example, one of skill in the art may (1) immunize an animal with an interleukin conjugated with ovalbumin in an amount to induce an immune response that inhibits the activity of the interleukin, (2) assay a parameter associated with a disorder that is dependent on a reduction in the activity of the interleukin before an agent to be assayed is administered to the immunized animal, (3) administer the agent to the immunized animal, (4) assay the parameter after the agent is administered, and (5) compare the parameter before and after the agent is administered to determine the effect of the agent. For example, the level of blood eosinophilia may be assayed in an animal immunized with IL-9-OVA before and after an agent is administered to determine if the agent affects the degree of eosinophilia. Blood eosinophils may be determined by, e.g., counting the cells on slides prepared by centrifugation of 30,000 Ficoll-purified leukocyte cells and staining with, e.g., Diff-Quik (Dade Behring, Deerfield, Ill.).

Those of skill in the art are aware of many methods that are useful for immunizing animals which need not be set forth herein. In the invention described herein, the animals are preferably immunized with 0.5–10 ug of an interleukin conjugate. The interleukin conjugates may be incorporated into any conventional pharmaceutically acceptable vehicle or diluent (see, e.g., Remington's Pharmaceutical Sciences ($19^{th}$ Ed) (Genarro, ed. (1995) Mack Publishing Co., Easton, Pa.)). For example, the conjugates may be administered with, e.g., buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary of suitable diluents. The conjugants may also be administered with an adjuvant. Preferred adjuvants are those used routinely in the art, e.g., Freund's Incomplete Adjuvant or Freund's Complete Adjuvant and Merck Adjuvant 65. Immunization with the conjugates may also be combined with the administration of other components involved with the recruitment of mast cells, eosinophils or TH2 cells, e.g., MCP-1, MCP-3, MCP-4, Eotaxin, MDC/TARC and 1-309, see U.S. Pat. No. 5,824,551.

Preferably, the adjuvantis Freund's complete orFreund's incomplete adjuvant and the innoculum comprises about 50% adjuvant (ratio of 1:1, adjuvant:composition). The animal may be immunized with the interleukin conjugate in a plurality of sequential innoculations. Preferably, the innoculations are given every 2 weeks for about 6 weeks. Although any amount of conjugate sufficient to induce an antibody response is suitable for inoculation, preferably each innoculum contains from about 1 ug to about 10 ug conjugate. Preferably, the innoculum contains an amount of about 2 ug of conjugate.

BRIEF DESCRIPTION OF THE FIGURES

FIGS. 1A and B depict induction of IL-9 specific autoantibodies.

DETAILED DESCRIPTION OF THE INVENTION

An in vivo system was designed to evaluate the efficacy of IL-9 vaccination for treating pathological conditions. The system is based on the immune response of mice to parasitic infections. IL-9 overproduction has been shown to promote rapid elimination of the caecal dwelling nematode *T.muris* (Faulkner, et al., *Infect. Immun.*, 66:3832–3840 (1998)). The results presented infra demonstrate that anti-IL-9 vaccination completely impaired worm expulsion and provided the first formal demonstration of a strict requirement for IL-9 in this process. Experiments carried out with monoclonal anti-IL-9 antibodies derived from mice immunized with IL-9-OVA confirmed this conclusion. The results also demonstrate that inhibiting IL-9 activity by immunizing animals with an IL-9-OVA conjugate or by administering IL-9-specific antibodies abrogates eosinophilia induced by parasitic infection or by implanted IL-9 secreting T-cells and thus provides evidence of the requirement for IL-9 in eosinophilia. The data presented herein demonstrate the potency of the strategy described herein for antagonizing IL-9 in vivo and demonstrate that this interleukin plays a major role in developing resistance against *T.muris* infection and the induction of blood eosinophilia.

Previous experiments have demonstrated that resistance to *T.muris* requires a Th2 reaction (Finkelman, et al., *Annu. Rev. Immunol.*, 15:505–533 (1997); Faulkner, et al., *Infect. Immun.*, 66:3832–3840 (1998)). Administration of IL-12 (Bancroft, et al., *Eur. J. Immunol.*, 27:866–870 (1997)) or of anti-IL-4 receptor antibodies prevents worm expulsion in otherwise resistant mice, while anti-IFNγ has curative activity in susceptible strains (Else, et al., *J. Exp. Med.*, 179: 347–351 (1994)). IL-13-deficient mice challenged with *T.muris* also fail to expel the parasite (Bancroft, et al., *J. Immunol.*, 160:3453–3461 (1998)). The present observation, that anti-IL-9 vaccination completely impairs worm expulsion, fits well with the notion that resistance to *T.muris* requires a Th2 reaction, since IL-9 is also a Th2 cytokine. In addition, as it has been reported that IL-9 production in response to *T.muris* is markedly reduced in IL-4- and in IL-13-knockout mice (Bancroft, et al., *J. Immunol.*, 160: 3453–3461 (1998)).

We assayed the effect of IL-9-OVA immunization on infections with nematode *Trichuris muris*. C57Bl/6 mice, which normally expel the parasite, became susceptible to infection after anti-IL-9 immunization. In addition, immunization with IL-9-OVA inhibited parasite-induced blood eosinophilia. These results demonstrate that IL-9 plays a critical role in *T. muris* infection and blood eosinophilia. However, inhibition of blood eosinophilia alone does not explain the effect of IL-9 immunization on susceptibility of mice to worm infection because anti-IL-5 antibodies, which also block eosinophilia, do not affect worm expulsion (Betts, et al., *Parasite Immunol.*, 21:45–52 (1999)). In addition, the IgE response and intestinal mast cell infiltration induced by the parasite were not impaired in IL-9-OVA vaccinated mice.

Using in vivo and in vitro assays, we demonstrate herein that immunization with conjugates of IL-9 and ovalbumin provide for a prolonged high titre production of IL-9 specific autoantibodies. The antibody titer in sera can be determined by various assays that are well known to those of skill in the art. For example, a high titer of antibodies specific for IL-9 according to this invention is about $10^{-3}$ to $10^{-5}$ as determined by an in vitro IL-9 dependent cell proliferation assay (e.g., Uyttenhove et al., *Proc. Natl. Acad. Sci. USA* 85:6934–6938 (1988)) reference. Other assays useful for determining the antibody titre to other interleukins, e.g., IL-4, IL-5 and IL-13 are known to the art and need not be set forth herein.

The conjugates of this invention are particularly suitable for the generation of polyclonal and monoclonal antibodies. General methods for the production of polyclonal and monoclonal antibodies are known in the art and thus need no further elaboration (see, e.g., U.S. Pat. No. 5,157,112; Kohler and Milstein, *Eur. J. Immunology*, 6:511–519 (1976); Kennett et al., *Monoclonal antibodies. Hybridomas: a new dimension in biological analyses* New York, Plenum 1980, all incorporated herein by reference). We produced neutralizing anti-IL-9 antibodies by immunizing mice with mouse IL-9 (mIL-9) coupled to ovalbumin. In the six mouse strains tested, a strong and long-lasting anti-IL-9 response developed with serum inhibitory titers of $10^{-3}$ to $10^{-5}$ as measured in an in vitro IL-9-dependent cell proliferation assay (Uyttenhove, et al., *Proc. Natl. Acad. Sci. USA*, 85:6934–6938 (1988)) described infra. In vivo, immunization with IL-9-OVA conjugates completely abrogated the increase in mast cell protease-1 (MMCP-1) levels as well as the eosinophilia observed in mice after implantation of an IL-9-secreting tumor. Anti-IL-9 vaccination thus provides a new tool to study IL-9 functions in vivo.

The antibodies produced by the methods of this invention that are specific for a cytokine are also useful in methods for treating pathological conditions which require, at least in part, the activity of the cytokine. Of six monoclonal antibodies assayed that are specific for IL-9, five were neutralizing. Neutralizing antibodies as disclosed herein reduce the activity of IL-9 in in vitro assays to levels that are not significantly different from the activity detected in control assays and in in vivo assays neutralizing antibodies significantly reduce one or more parameters associated with a pathological condition in an animal as compared to control animals having the pathological condition. For example, the neutralizing monoclonal antibodies described herein successfully prevented eosinophilia in mice wherein the eosinophilia was induced by an implanted IL-9-secreting cell line.

Immunization with mouse IL-9 chemically complexed to OVA induced high titers of neutralizing anti-IL-9 antibodies in the six mouse strains tested, regardless of their IL-9 production levels. Mice immunized with IL-9 simply mixed with OVA and adjuvant failed to produce neutralizing anti-IL-9 antibodies demonstrating that proper covalent complex formation is essential. Moreover, immunization with IL-9 cross-linked to OVA through carbodilmide or bis-diazobenzidine did not induce production of neutralizing anti-IL-9 antibodies. Of note, these complexes failed to sustain IL-9 dependent cell growth in vitro, suggesting that modification of certain carboxyl and tyrosyl groups altered critical IL-9 epitopes. By contrast, IL-9-OVA complexes produced with glutaraldehyde still sustained cell proliferation.

The mere polymerization of IL-9 with glutaraldehyde was unable to break B cell tolerance indicating that IL-9 polymers alone, even very large in size (60–1000 kD), are not sufficient to induce an anti-IL-9 response. This is in contrast to the response of transgenic mice, transgenic for vesicular stomatitis virus G-protein (VSV-G), which mount a Tcell-independent IgM response against VSV-G when the protein is presented in a highly repetitive structure (on whole virions) but not in free form, soluble orat low concentrations on cell surfaces (Bachmann et al., *Science*, 262:1448–1451 (1993)). Moreover, the induction of anti-IL-9 autoantibodies is probably T cell-dependent because most of the anti-IL-9 autoantibodies are IgGs.

The results disclosed herein demonstrate that anti-IL-9 vaccination blocks IL-9 activities in vivo and demonstrates that IL-9 is required for *T. muris* expulsion and eosinophilia.

These findings suggest that IL-9 immunization can be used to limit adverse consequences of IL-9 production, in pathologies involving eosinophil-mediated toxicity, e.g., allograft rejection (Le Moine, et al., *J. Clin. Invest.*, 103: 1659–1667 (1999); de Groen, et al., *Hepatology*, 20:654–662 (1994); and Martinez, et al., 55:909–918 (1993)) and in asthma(Temann, supra; McLane, et al., *Am. J. Resp. Cell. Mol.*, 19:713–720 (1998), and Nicolaides, et al., *Proc. Natl. Acad. Sci. USA*, 94:13175–13180 (1997)). These results also suggest that inhibiting the activity of other interleukins, wherein the interleukin is involved in the initiation or progression of a pathological condition may be beneficial for eliminating or reducing the symptoms of the condition.

The following examples are offered by way of illustration, and not by way of limitation. Those skilled in the art will recognize that variations of the invention embodied in the examples can be made, especially in light of the teachings of the various references cited herein.

EXAMPLES

Example 1

Immunization with IL-9: In Vitro Assays

A. Mice and Parasites

All mice used in this study were females bred and housed under pathogen-free conditions. The maintenance of *Trichuris muris* and the method used for infection and evaluation of worm burden were as described by Wakelin (Wakelin, *Parasitology*, 57:515–524 (1967), incorporated herein by reference). Mice were infected with approximately 200 eggs, and bled or sacrificed at various time points after infection, as described in the text.

B. Cell Culture and Cytokines

Dulbecco's modified Eagle's medium supplemented with 10% fetal calf serum, 50 μM 2-mercaptoethanol, 0.55 mM L-arginine, 0.24 mM L-asparagine, 1.25 mM L-glutamine was used for all experiments.

Recombinant murine IL-9 and IL-4 were purified from baculovirus-infected Sf9 insect cell cultures, as previously described (Druez, et al., *J. Immunol.*, 145:2494–2499 (1990), incorporated herein by reference). The supernatant of DBA/2 spleen cells cultured for 48 hours in the presence of 1 ng/ml of phorbol 12-myristate 13-acetate (Sigma) and 200 ng/ml of calcium ionophore A23187 (Sigma) was used as a source of natural mouse IL-9.

C. Preparation of IL-9-OVA Complexes and Immunization Protocol

IL-9-OVA complexes were prepared by cross-linking mouse IL-9 and ovalbumin with glutaraldehyde. The reaction was carried out with shaking in 0.1M phosphate buffer pH7, first at room temperature for 3 hrs, then overnight at 4° C., by mixing equimolar amounts of purified recombinant murine IL-9 and OVA with glutaraldehyde at a final concentration of 50 mM.

The complexed proteins were separated from the starting material by size exclusion chromatography on a Superose column (Pharmacia) equilibrated in PBS supplemented with Tween 20 ($10^{-4}$; v/v) and 0.2 M NaCl. IL-9-OVA complexes were detected in column fractions by ELISA using a hamster monoclonal antibody, specific for IL-9, and rabbit anti-OVA antiserum, followed by peroxidase-conjugated anti-rabbit antibody for detection of complexes. The size of the conjugates ranged from 60 kD to greater than 1000 kD, as observed in SDS-PAGE. For immunization, all material containing IL-9 with a size exceeding 60 kD was pooled.

Eight-week old C57Bl/6, Balb/c, NOD, and NZW mice were primed subcutaneously in the tail with a 100-μl 1/1 mixture of complete Freund's adjuvant (CFA) and complexed proteins in PBS (depending on the experiment 1, 2, 5, or 10 μg IL-9-OVA complex). Two subcutaneous boosts were performed with the same quantity of antigen, mixed 1/1 with incomplete Freund's adjuvant (IFA), 2 weeks and 4 weeks after the initial injection. Blood samples were taken from the mice 15 days after the second boost. Control mice received either an equivalent amount of OVA in Freund's adjuvant or adjuvant alone.

D. Detection of Anti-IL-9 Antibodies

Anti-IL-9 antibody titers were measured by assaying the inhibitory activity of the sera on the proliferation of TS1 cells that respond to IL-9 and IL-4 (Uyttenhove et al., *Proc. Natl. Acad. Sci. USA*, 85:6934–6938 (1988), incorporated herein by reference). In this assay, one interleukin unit/ml, defined as the concentration required for half-maximal proliferation, corresponds to 25 pg/ml for IL-9 and 250 pg/ml for IL-4, respectively. Sera were serially diluted in 96-well plates containing culture medium and incubated in the presence of 2.5 U/ml murine IL-9 (mIL-9) or murine IL-4 (mIL-4) for one hour. TS1 cells were extensively washed and 2500 cells added per well. The cells were then incubated at 37° C., 8% $CO_2$ for 3 days and cell proliferation was measured by determining the hexosaminidase activity (Landegren, *J. Immunol. Method*, 16:67:379–388 (1984), incorporated herein by reference).

E. Spontaneous and Specific Immunoglobulin Production

The baseline serum immunoglobulin (Ig) levels in groups of five 20-week-old IL-9-OVA immunized or control C57Bl/6 mice were measured as previously described (Coutelier, et al., *J. Virol.*, 64:5383–5388 (1990), incorporated herein by reference). Three weeks after the last boost with IL-9-OVA or CFA, antigen-specific responses were induced in BalbC mice by intraperitoneally injection of *Aspergillus* protein (200 ug) in alum (2.25 mg) twice a week for, 4 weeks. Anti-*Aspergillus* IgG1 and IgE antibodies, as well as total IgE, which is increased in response to *Aspergillus*, were measured by ELISA. To determine the specificity of the antibodies, microtiter plates were coated with *Aspergillus* antigen (10 ug/ml) in 20 mM glycine buffer containing 30 mM NaClpH9.2 and incubated overnight at 4° C. After washing in 0.1 M NaCl plus Tween 20 ($5 \times 10^{-4}$), serial dilutions of samples were added and plates were incubated for 2–3 hours at 37° C. Plates were then washed as before and soaked for 7 min. in 0.1 M NaCl containing Nonidet-P40 1% before further incubation. Bound IgG and IgE were detected using rat anti-IgG1 or anti-IgE monoclonal antibodies coupled to peroxidase. The assay was developed by adding 2,2'-azino-bis-(3-ethyl benzthiazoline 6 sulfonic acid) ("ABTS") following manufacturer's instructions. Absorbance at 405 nm was measured and non-saturating serum dilutions were compared for analysis.

F. Blood Leukocyte Population Analysis and Eosinophil Counts

Blood leukocyte populations were analyzed ten months after the last boost in C57Bl/6 mice immunized with IL-9-OVA (4 mice) or vehicle (4 mice). Briefly, heparinized blood samples were centrifuged on a Ficoll layer and incubated for 6 minutes in 0.15M $NH_4Cl$ for red blood cell lysis. Cells were labeled with FITC-coupled anti-CD4 or anti-CD8 antibodies biotinylated rat anti-Mac-1 antibodies followed by PE-conjugated streptavidin and FITC-conjugated anti-IgM. After staining, cells were fixed in paraformaldehyde (1.25%) and fluorescence intensity was measured, using 10,000 cells/sample in a FACScan™ apparatus.

Blood eosinophils were counted on slides prepared by centrifugation of 30,000 Ficoll-purified leukocyte cells and staining.

G. MMCP-1 ELISA

Serum levels of MMCP-1 were measured using a commercially available MMCP-1 ELISA kit, as described in Faulkner, et al ., *Infect. Immun.*, 66:3832–3840 (1998), incorporated herein by reference. Briefly, rabbit anti-MMCP was used as capture antibody. Tenfold serial dilutions (1/10 to 1/10,000) of serum were prepared, a horseradish peroxidase conjugated rabbit anti-mouse MMCP-1 was added and serum levels of MMCP-1 were quantified by comparing to a purified MMCP-1 reference. Assays were developed as described above for Ig ELISAs.

H. Histology

The caecum tip was removed at autopsy from *T.muris* infected animals (21 days post-infection) and fixed in Carnoy's fluid for 5 hours (for mast cell counts) or in 4% neutral buffered formalin for 24 hours (for eosinophil counts), prior to processing by standard histological techniques. For mast cell enumeration, sections were stained in 0.5% toluidine blue (pH 0.3) and for eosinophils, slides were incubated in 0.5% chromotrope 2R containing 1% phenol. The number of cells was determined in 20 caecal-crypt units per animal.

I. Statistical Analysis

Statistical analysis was performed using the Mann-Whitney U test, with P values below 0.05 considered significant. The Mann-Whitney U test is a well-known non-parametric statistical procedure that can be used to test treatment effects. The Mann-Whitney U test, which may also be referred to as the Wilcoxon-Mann-Whitney test, or the Wilcoxon Rank-Sum test, evaluates the ranks of the combined scores from two independent groups.

Example 2

IL-9 Immunization: In Vitro Assays

Groups of four C57Bl/6 mice were injected subcutaneously with IL-9-OVA complexes in CFA (IL-9–OVA), with noncomplexed IL-9 and OVA (IL-9+OVA) or with CFA alone (CFA). Boosts were carried out in IFA after 2 and 4 weeks. Serially diluted sera, collected 2 weeks after the last boost, were tested for IL-9 inhibition in a TS1 cell proliferation assay described supra. Cell growth was evaluated by measuring hexosaminidase activity. Means±SD are indicated in FIG. 1A.

C57Bl/6 mice were immunized with three injections species two weeks apart cross-linked to OVA of IL-9. Two weeks after the last injection, the anti-IL-9 response was evaluated by measuring serum inhibitory activities in a bioassay, using IL-9-dependent T cell line TS1. FIG. 1A demonstrates that the sera were found to strongly inhibit IL-9-induced proliferation, the half-maximal inhibition of 2.5 U/ml murine (mIL-9) being obtained at serum dilutions ranging from $10^{-4}$ to $10^{-5}$. Sera from mice immunized with non-complexed IL-9 and OVA, or with adjuvant only, had no inhibitory activity. Since the immunization and the IL-9 assay were carried out with recombinant IL-9 produced in baculovirus-infected Sf9 insect cell cultures (Druez, et al., *J.*

*Immunol.*, 145:2494–2499, (1990) supra), it was important to verify that the sera also inhibited natural murine IL-9.

Figure 1:
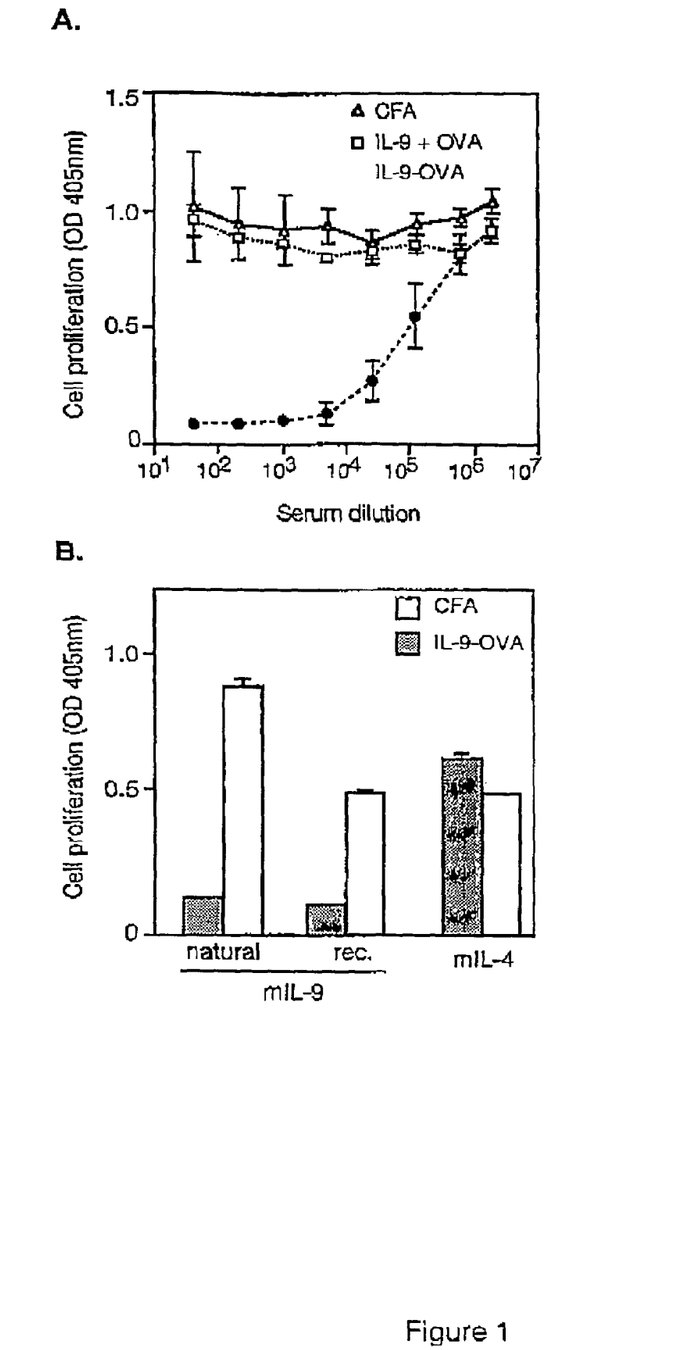

FIG. 1B demonstrates the specificity of anti-IL-9 activity. Pools of 1/320 diluted sera from immunized (IL-9-OVA) or control (CFA) mice were tested for growth inhibition of TS1 cells, in the presence of either natural mIL-9 or baculovirus-derived recombinant mIL-9 ("rec" in FIG. 1B) or mIL-4. Cell proliferation was measured after 3 days of culture. Results are given as means±SD. As shown in FIG. 1B, both forms of IL-9 were inhibited, while IL-4, which also stimulates TS1 cell proliferation, was not, thus providing clear proof of anti-IL-9 specificity. Dose-response analyses showed that optimal antibody responses were obtained with 3 injections of 2 ug complexes. Increasing the amount of injected material to 10 μg did not increase inhibitory titers (data not shown).

Figure 2:
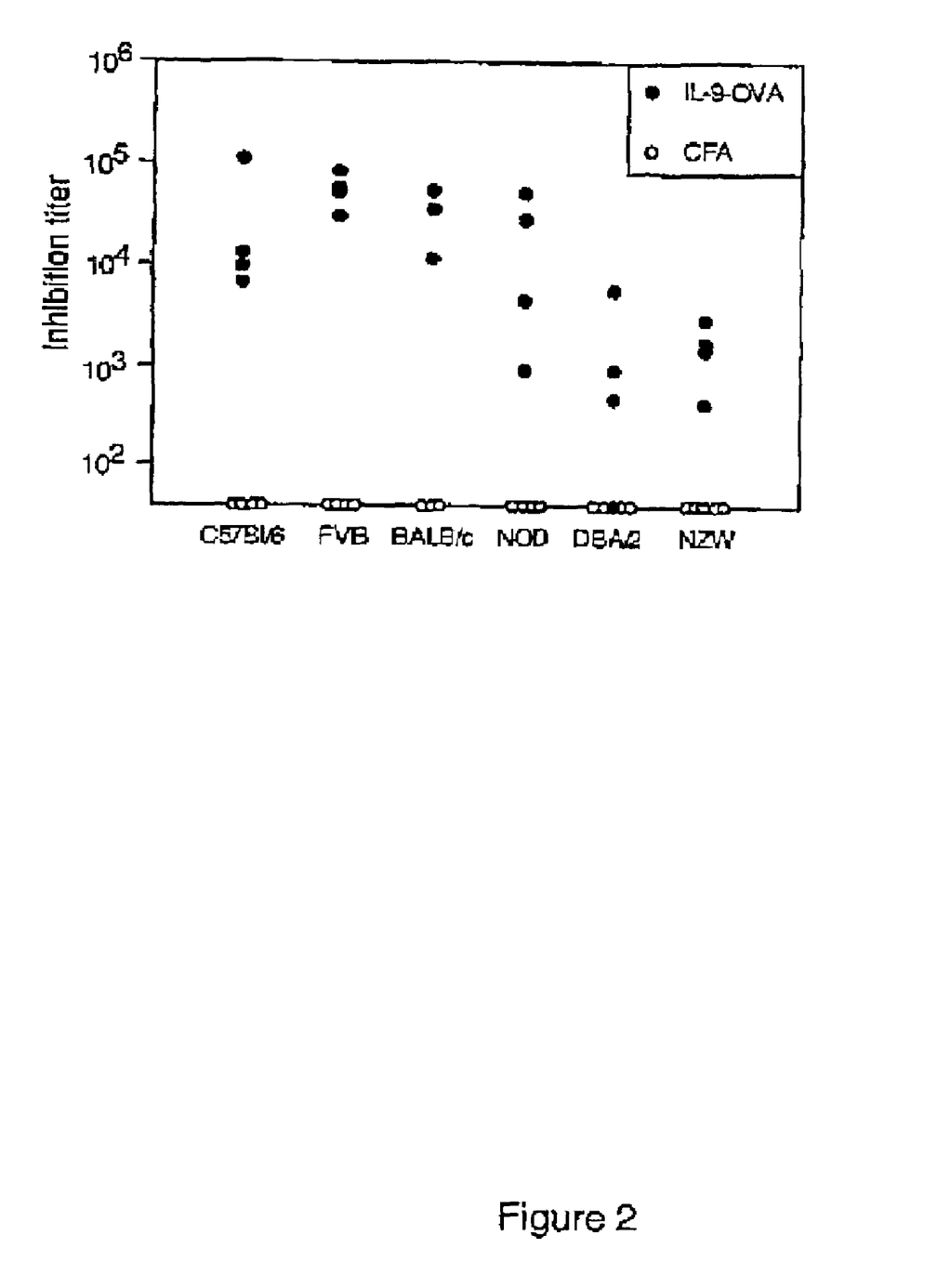
FIG. 2 depicts the production of anti-IL-9 autoantibodies in different mouse strains.

Because C57Bl/6 mice have been reported to be low IL-9 producers (Nicolaides, et al., *Proc. Natl. Acad. Sci. USA*, 94:13175–13180 (1997)), other mouse strains were immunized as well. FIG. 2 depicts the product-ion of anti-IL-9 autoantibodies in different mouse strains. Eight week-old C57Bl/6, FVB, Balb/c, NOD, DBA/2 and NZW mice were injected with IL-9-OVA complexes (4 mice) or adjuvant only (4 mice), as described supra. Serially diluted sera, collected 2 weeks after the last immunization, were tested in a TS1 cell proliferation assay. Inhibition titers, given for each mouse serum, correspond to serum dilutions inhibiting IL9-induced cell proliferation by 50%. The results demonstrate that immunization of FVB, NOD, Balb/c, DBA/2 and NZW mice with IL-9-OVA complexes induces very significant anti-IL-9 responses in all strains tested, demonstrating the general applicability of the immunization protocol.

Figure 3:
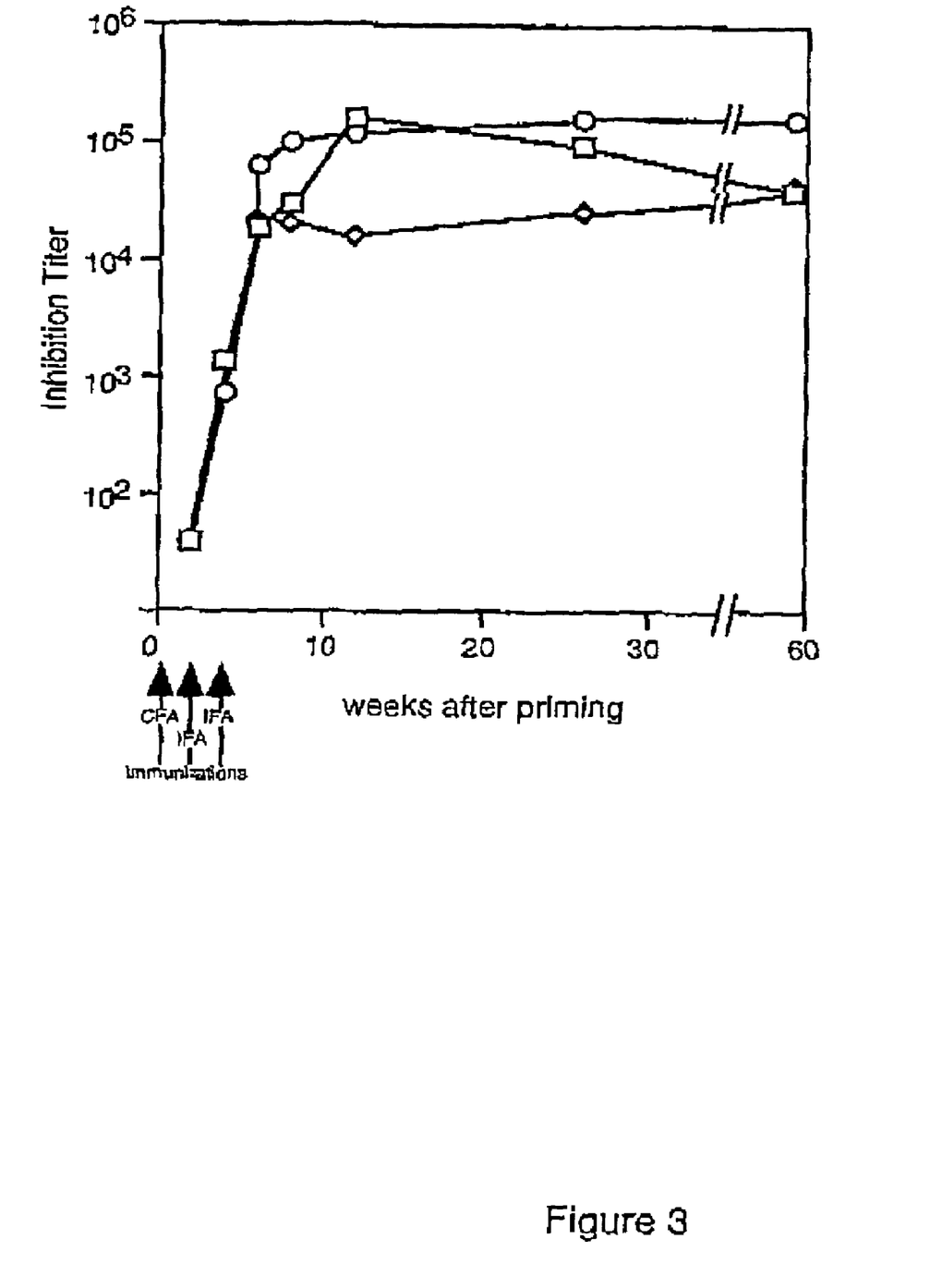
FIG. 3 depicts the persistence of the anti-IL9 response in immunized mice.

FIG. 3 demonstrates the persistence of the anti-IL9 response in immunized mice. Three 8 week-old C57Bl/6 mice were injected subcutaneously with IL-9-OVA complexes in CFA. Mice were boosted with IFA after 2 and 4 weeks. Serum was collected 2, 4, 6, 8, 12, 26, and 56 weeks after priming and assayed for anti-IL-9 activity in a TS1 cell proliferation assay. The results are given as the inhibition titer for individual mouse sera. A striking feature of the anti-IL-9 response was its persistence (FIG. 3). In fact, titers remained elevated for more than a year after the immunization at 4 weeks, suggesting that the vaccinated animals could be used to evaluate the consequences of long-term IL-9 blockade in vivo.

Example 3

Inhibition of IL-9-Induced Mast Cell Activation and Eosinophilia in IL-9-Vaccinated Mice.

Figure 4:
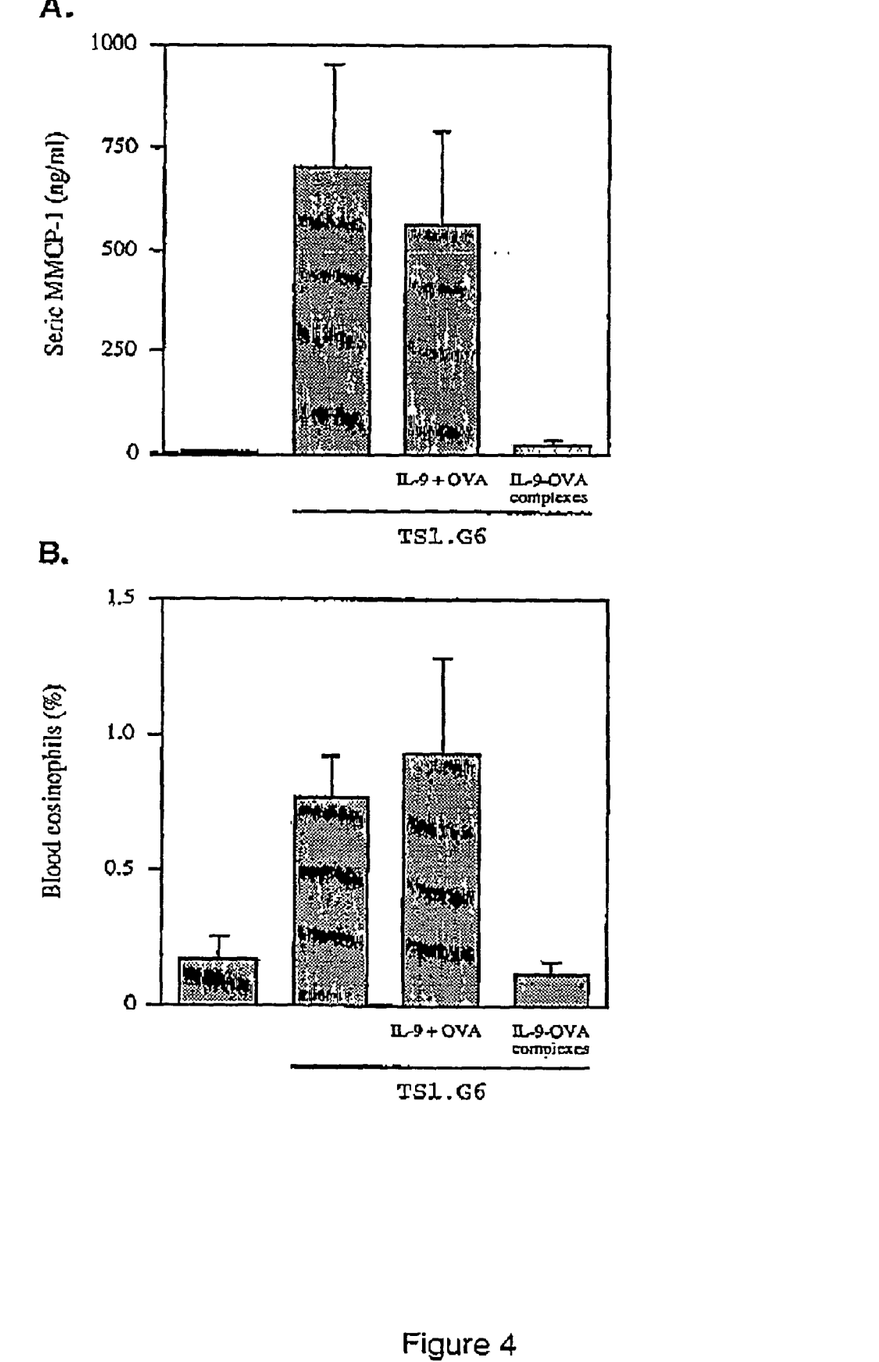
FIGS. 4A and 4B depict the inhibition of IL-9-induced mast cell activation and eosinophilia in immunized mice.

An IL-9-secreting T cell line, able to grow in C57Bl/6 mice, was used to raise IL-9 levels in vivo. This cell line, TS1.G6, secretes±1 ng IL-9/$10^6$ cells/48 h in vitro (Uyttenhove, et al., *J. Exp. Med.*, 173:519–522 (1991)) andhas previously been shown to induce high serum levels of MMCP-1 (Faulkner, et al., (1998) *Infect. Immun.*, 66:3832–3840). Seven week old C57Bl/6 mice were immunized with either IL-9-OVA complexes or uncomplexed IL-9 and OVA as described supra. Five months after the last boost $10^7$ TSI.G6 cells were injected into the peritoneal cavity of the untreated C57Bl/6 control mice or mice immunized either with the IL-9-OVA complexes or uncomplexed IL-9 and OVA. In both the untreated age-matched negative control mice and the mice inmunized with uncomplexed IL-9 and OVA, MMCP-1 concentrations, measured 25 days after TS1.G6-inoculation, rose from 6 ng/ml in non-tumor-bearing mice to 700 ng/ml. By contrast, in mice immunized with IL-9-OVA complexes, MMCP-1 concentrations remained as low as 20 ng/ml (P=0.03; FIG. 4A).

In addition to increasing MMCP-1 serum levels, TS1.G6 inoculation also raised the percentage of eosinophils in peripheral blood leukocytes from 0.16±0.10 to 0.77±0.15 (P=0.016). This eosinophilia was completely abrogated in mice immunized with IL-9-OVA complexes (0.11±0.05%; P=0.02) but not in mice immunized with non-complexed IL-9 and OVA (0.93±0.35%) (FIG. 4B).

Analysis of body weight, basal immunoglobulin levels and peripheral blood leukocyte composition showed no significant anomalies in unchallenged vaccinated animals (data not shown).

The influence of anti-IL-9 vaccination on non-specific antibody responses was also evaluated. Balb/c mice, immunized with IL-9-OVA for two months, were challenged with *Aspergillus fumigatus* antigen. Both anti-*Aspergillus* IgG1 and IgE responses developed similarly in vaccinated and control animals (P>0.05; Table 1), indicating that anti-IL-9 immunization did not interfere with the development of normal antibody responses and did not prevent anti-*Aspergillus* IgE production.

TABLE 1

Normal antibody responses against Aspergillus antigen in IL-9-OVA-immunized Balb/c mice.

| Immunization | Plate | IgG1 | IgE |
|---|---|---|---|
| Vehicle | Aspergillus | 0.363 ± 0.002 | 0.428 ± 0.023 |
| | BSA | 0.054 ± 0.001 | 0.109 ± 0.006 |
| LL-9-OVA | Aspergillus | 0.227 ± 0.055 | 0.363 ± 0.083 |
| | BSA | 0.046 ± 0.003 | 0.117 ± 0.028 |

Anti-*Aspergillus* IgG1 and IgE were detected in sera from control or IL-9-OVA immunized Balb/c mice injected with *Aspergillus fumigatus* extracts (4 mice per group). The values correspond to absorbance units at 405 nm measured at non-saturating serum dilutions (1/2500 for IgG1 and 1/20 for IgE) on plates coated with *Aspergillus* antigen or BSA as a control. Mean±SEM are indicated.

Example 4

Inhibition of *T.muris* Expulsion by Anti-IL-9 Vaccination

The preceding results demonstrated the ability of anti-IL-9 vaccination to interfere with IL-9 activities in vivo and suggest that this procedure can be used to unravel new IL-9 biological functions. TS1.G6 cells as well as IL-9 transgenic mice have previously been used to show that IL-9 can enhance resistance to the intestinal helminth *T.muris* (Faulkner, et al., *Infect. Immun.*, 66:3832–3840 (1998)). IL-9-vaccinated animals provided the opportunity to test the actual requirement for IL-9 in a resistant strain.

C57Bl/6 mice under normal circumstances rapidly expel the parasite. C57Bl/6 mice immunized with IL-9-OVA complexes or vehicle (eight mice per group) were infected by oral lavage of 200 *T.muris* eggs. Worms were counted in caeca on day 34 after infection and results are given as worm burden in each individual. P value between groups is 0.001. On day 13, the worm burden, assessed to verify infectivity, was similar in all aninals.

Figure 5:
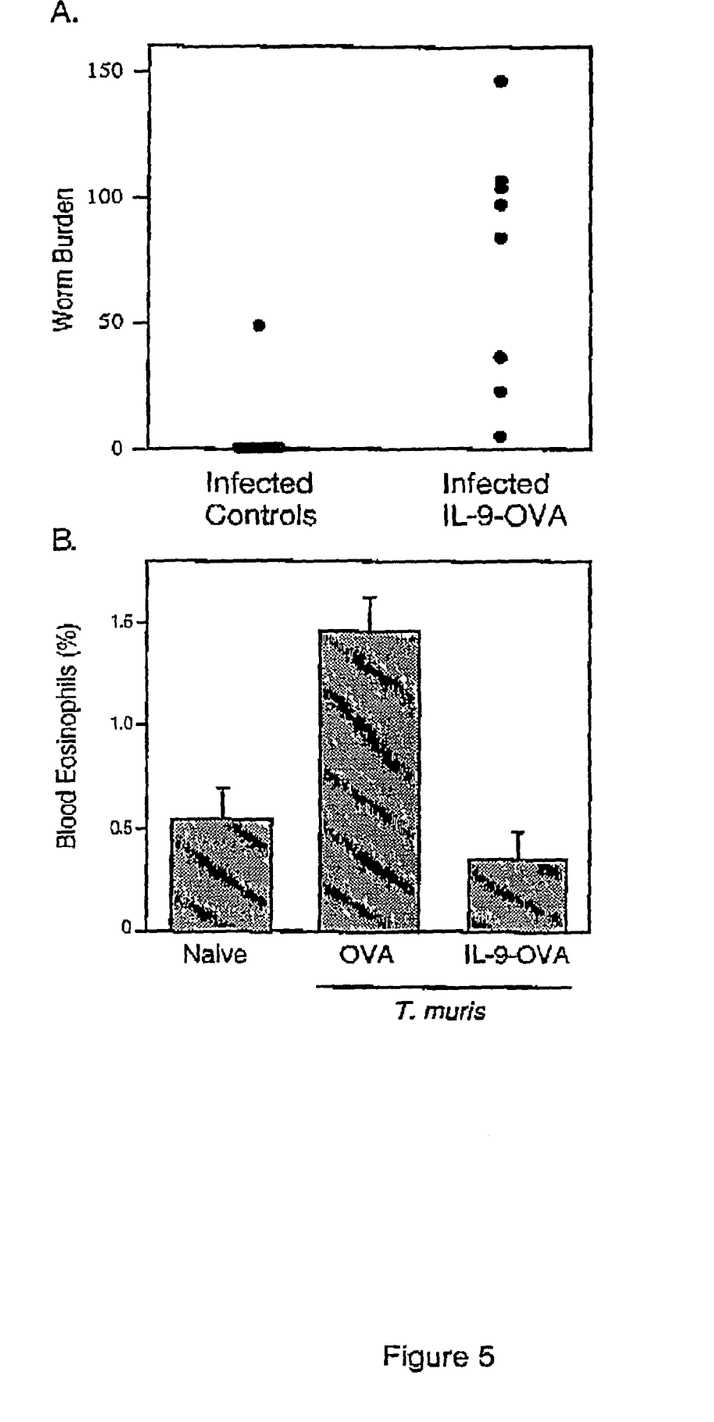
FIGS. 5A and 5B depict the failure of IL-9-OVA-immunized C57Bl/6 mice to expel *T.muris* and the inhibition of *T.muris*-induced blood eosinophilia in IL-9-vaccinated mice.

As shown in a representative experiment (FIG. 5A), anti-IL-9 vaccinated animals failed to expel the parasite by this time, while 7 of the 8 control mice were parasite-free. Blood eosinophils were counted 23 days post-infection from infected control or IL-9-OVA vaccinated C57Bl/6 mice, or uninfected naive animals. Eosinophil percentages were determined by enumerating 500 cells per slide. Results are presented as the mean percentage of blood eosinophils±SEM (4 mice per group). P value is 0.029 for the difference between OVA and IL-9-OVA groups. Blood eosinophilia induced by the infection was totally abrogated in the immunized mice (FIG. 5B). By contrast, caecal eosinophil and mast cell accumulations were increased in vaccinated animals, although not to the point to reach statistical significance (P>0.05; Table 2). Also, total IgE serum concentrations were similarly increased in OVA- or IL-9-OVA-vaccinated animals (data not shown).

TABLE 2

Normal intestinal mastocytosis and eosinophil infiltrates induced by *T. muris* infection in IL-9-OVA-immunized mice.

| T. muris | Immunization | Mast cells | Eosinophils |
|---|---|---|---|
| − | — | 2 ± 1 | 8 ± 1 |
| + | OVA | 88 ± 63 | 56 ± 11 |
| + | IL-9-OVA | 201 ± 44 | 110 ± 11 |

Mast cells and eosinophils were counted in caeca, 21 days after Infection with *T.muris*, in C57Bl/6 mice immunized with OVA or IL-9-OVA complexes or in uninfected animals (4 mice per group). Results are presented as mean number of cells (±SEM) per 20 caecal-crypt units.

Example 5

Inhibition of Eosinophilia by Monoclonal Antibodies Specific for IL-9

To determine the ability of monoclonal antibodies to block eosinophilia, IL-9 secreting cells ($10^7$cells) were injected into C57Bl/6 mice. Four weeks after the injection the eosinopril counts were 1.5±0.1%, determined as described supra. Two days later 1 mg of monoclonal antibodies specific for IL-9 (either MM9A1, an IgG1, or MM9A4, an IgG2a) were injected into the mice. Control mice received similar amounts of IgG1 and IgG2a that were not specific for IL-9. After six days, the eosinophil count was assayed and found to be <0.2% in the anti-IL-9-treated mice and 1.2±0.52 in the control mice.

The forgoing results further extend the efforts made to generate autoantibodies capable of regulating biological processes. The results demonstrate a role for IL-9 in blood eosinophilia and also demonstrate that the induction or administration of antibodies specific for IL-9 abrogates eosinophilia, suggesting potential benefits for anti-IL-9vaccination in pathologies involving eosinophil-mediated toxicity, e.g., allograph rejection.

The foregoing examples are offered by way of illustration, and not by way of limitation, and demonstrate the efficacy of producing antibodies specific for a cytokine, particularly an interleukin, and to a method to treat a pathological condition that is dependent at least in part on the activity of the particular cytokine. Those skilled in the art will recognize that variations of the invention embodied in the examples can be made, especially in light of the teachings of the various references cited herein.

The invention claimed is:

1. A method for inhibiting interleukin-9 (IL-9) activity in a subject suffering from a condition selected from the group consisting of excess lymphomagenesis, intestinal mastocytosis, overexpansion of β1 lymphocytes, and bronchial hyperresponsiveness, comprising administering an amount of a conjugate of IL-9 and a carrier to said subject, in an amount sufficient to induce production of antibodies which bind to and neutralize IL-9, and to alleviate said condition.

2. The method of claim 1, wherein said carrier is ovalbumin, keyhole limpet hemocyanin, acetylated bovine serum albumin, or Bortadella pertussis toxin.

3. The method of claim 2, wherein said ovalbumin is maleimide substituted ovalbumin, conjugated to IL-9 via a free SH group in said IL-9.

4. The method of claim 2, wherein said carrier is cross-linked to IL-9 via glutaraldehyde.

5. The method of claim 1, wherein said subject is a mammal.

6. The method of claim 1, comprising administering said conjugate to said subject at intervals of about 2 weeks, for a period of about 6 weeks.

7. The method of claim 1, comprising administering said conjugate in an amount ranging from about 1 μg to about 10 μg.

8. The method of claim 1, wherein said condition is bronchial hyperresponsiveness.

9. The method of claim 1, wherein said condition is excess lymphomagenesis.

10. The method of claim 1, wherein said condition is intestinal mastocytosis.

11. The method of claim 1, wherein said condition is overexpansion of β1 lymphocytes.

12. The method of claim 8, wherein said conjugate comprises IL-9 and ovalbumin.

13. A method for inducing an elevated titer of an antibody which is specific for and neutralizes interleukin-9 (IL-9), comprising administering to a subject an amount of a conjugate of IL-9 and a carrier in an amount sufficient to provoke production of antibodies which are specific to IL-9 wherein the elevated titer of said antibody persists for at least six months following immunization.

14. The method of claim 13, wherein said carrier is selected from the group consisting of ovalbumin keyhole limpet hemocyanin, acetylated bovine serum albumin, and Bortadella pertussis toxin.

15. The method of claim 14, wherein said ovalbumin is maleimide substituted ovalbumin, conjugated to IL-9 via a free SH group in said IL-9.

16. The method of claim 15, wherein said carrier is cross linked to IL-9 via gluteraldehyde.

17. The method of claim 13, wherein said subject is a mammal.

18. The method of claim 13, comprising administering said conjugate to said subject at intervals of about 2 weeks, for a period of about 6 weeks.

19. The method of claim 13, comprising administering said conjugate in an amount ranging from about 1 μg to about 10 μg.

* * * * *